United States Patent
Greenwood et al.

(12)

(10) Patent No.: US 6,174,705 B1
(45) Date of Patent: Jan. 16, 2001

(54) ARO1 DEHYDROQUINATE SYNTHASE OF CANDIDA ALBICANS

(75) Inventors: Rebecca Greenwood, Berwyn; Richard Nicholas, Collegeville, both of PA (US)

(73) Assignee: SmithKline Beecham Corporation, Philadelphia, PA (US)

(*) Notice: Under 35 U.S.C. 154(b), the term of this patent shall be extended for 0 days.

(21) Appl. No.: 09/425,665

(22) Filed: Oct. 22, 1999

(51) Int. Cl.[7] .............................. C12N 1/21; C12N 15/31; C12N 15/52; C12N 15/62; C12N 15/63
(52) U.S. Cl. .................. 435/69.1; 435/320.1; 435/252.3; 435/254.11; 435/325; 435/455; 435/471; 536/23.1; 536/23.2; 536/23.4; 536/23.7; 536/23.74; 514/44
(58) Field of Search .............................. 536/23.74, 23.1, 536/23.2, 23.4; 435/183, 320.1, 252.3, 254.11, 325, 455, 471, 69.1; 530/350; 514/44

(56) References Cited

PUBLICATIONS

Lambert, et al: "The 3–dehydroquinate synthase activity of the pentafunctional arom enzyme complex of the *Neurospora crassa* is $Zn^{2+}$ –dependent." *Biochemical Journal* vol. 226, pp. 817–829, 1985.*

Duncan, et al: "The pentafunctional aron enzyme of *Saccharomyces cerevisiae* is a mosaic of monofunctional domains." *Biochemical Journal*, vol. 246, pp. 375–386, 1987.*

Lamb, et al: "In vivo overproduction of the pentafunctional arom polypeptide in *Aspergillus nidulans* affects metabolic flux in the quinate pathway." *Molecular and General Genetics*, vol. 227, pp. 187–196, 1991.*

Banjeri, et al: "The Cloning and Characterization of the arom gene of *Pneumocystis carinii*." *Journal of General Microbiology*, vol. 139, pp. 2901–2914, 1993.*

Graham, et al: "Over–expression of the yeast multifunctional arom protein." *Biocheimica Biophysica Acta*, vol. 1216, pp. 417–424, 1993.*

Hawkins, et al: "The molecular biology of the pentafunctional AROM protein." *Biochemical Soceity Transactions*, vol. 21, pp. 181–186, 1993.*

* cited by examiner

*Primary Examiner*—Scott D. Priebe
*Assistant Examiner*—Peter Brunovskis
(74) *Attorney, Agent, or Firm*—Edward R. Gimmi; Thomas S. Deibert; William T. King

(57) ABSTRACT

The invention provides ARO1 polypeptides and DNA (RNA) encoding such ARO1 and a procedure for producing such polypeptides by recombinant techniques. Also provided are methods for utilizing such ARO1 for the treatment of infection, particularly fungal infections. Antagonists against such ARO1 and their use as a therapeutic to treat infections, particularly fungal infections are also provided. Further provided are diagnostic assays for detecting diseases related to the presence of ARO1 nucleic acid sequences and the polypeptides in a host. Also provided are diagnostic assays for detecting polynucleotides encoding arom and for detecting the polypeptide in a host.

21 Claims, No Drawings

SEQUENCE LISTING

<160> NUMBER OF SEQ ID NOS: 2

<210> SEQ ID NO 1
<211> LENGTH: 4656
<212> TYPE: DNA
<213> ORGANISM: Candida albicans

<400> SEQUENCE: 1

```
atgtctattg aaaaggtgcc aattttgggt aaggaaacta tccatgttgg ttatggtatt        60
gccgaccata ttgtcaggga agtgatagcc aacttggctt cttcaactta tgttatagtg       120
actgacacaa acatggcaag aactccccaa tattccaaat tgactgatga tttcaaaact       180
aatttgtctg aaaaacgtcc tgaatccaga ttattgactt attgtgtatc accgggtgaa       240
aacaacaaaa acagagctac caaagctgca gtggaagatt ttcttttaca acaaggttgt       300
accagagaca ccgtcatatt ggctgttggt ggggggtgtta ttggtgacat gattgggttt       360
gttgccgcca catttatgag aggtgtcaga gttgttcaag ttccaactac attgttagcc       420
atggtagatt catctgttgg tgggaaaacc gccattgata ctccattagg taagaatttc       480
attggtgctt tccatcaacc cgaatacgtt ttctgtgatg tatccttttt agagacttta       540
cctgctagac aatttattaa tggtatggct gaagttgtga aaactgcggc catttggaat       600
gaagaagaat tcaccagatt agaaaacttt tccaagaagt ttctttctgt cgttacctcc       660
aaaaaaccag atttacagtc aattaaggct gaattagtga aaaccgtttt ggaatctgtt       720
agagtgaaag ctggtgttgt gtcatctgat gaaaaggaag ctggtcttag aaatttactt       780
aattttggcc atactattgg tcatgcaatt gaagcggttt taactccaga agcattacat       840
ggagaatgtg tttctattgg tatgattaag gaagctgagt tgtctagata tttgggtata       900
ctaccacctg ttgcagttgc cagattgtcg aaatgtctcg ttgcttacgg cttacctgtg       960
tctattgacg ataaagaatt cttgaaaaaa gtgggaccaa aacgtcatta tgttgaaatc      1020
gatattttgt tgaaaaaaat ggccattgac aagaaaaatg atggtagtaa gattagatgt      1080
gtcttgttag agaaaattgg taaatgttac caattgaaag cacatcaagt atccaaacaa      1140
gatttaagtt ttgtgttgac tgatgaagtg ttggttcacc cattcaccaa tccacctaaa      1200
gaaaacataa ttgttccacc tggttccaaa tctatctcca atagagcatt gattttagct      1260
gctttgggta atggtactgt tcgtgtgaaa aatttgttac attcagacga tactaagcat      1320
atgttagatg ctgttgcttc tttaagggga gctgaaatat ccactgaaga taatggtgaa      1380
accattgtag ttaaaggaaa tggtggcaac ttggtcacat ctggcgaaga attgtacttg      1440
ggtaatgctg gtactgcttc cagatttttg actactgtag cttcattagt gggcaaatca      1500
caagctagtg atgatgttat tttaactggt aacgcaagaa tgcaagaaag acctattgga      1560
ccattagtgg atgccttggg atctaatggt tctgagattg agtatttgaa taagcagggt      1620
```

```
tcattgccat tgaaaatcag tgctggcaat ggattgaaag gtggaagaat agaattggct    1680
gcaacaatct cttcgcagta tgtttcttca attttaatgt gtgcaccata tgctaaggag    1740
ccagttactt tggctttagt cggaggtaaa ccaatttctc aattatacat agatatgaca    1800
tgtgcaatga tgaaatcatt tggtattgaa gttaccaaat caactactaa ggaatacacc    1860
tatcatattc caaaggggac atacaagaat ccatctgaat atgtcattga atcagatgcg    1920
tcatctgcaa cttatccatt agcatttgct gctatgactg aacatcctg tactattccg     1980 aacataggtt cttcctcatt acaaggagat gccaaatttg ctgttgatgt gttgaaacca    2040
atggggtgta agttgaaca aaccacaact tcaacaactg taactggtcc gccgagaggt     2100
cacttgaaac cattacctca tgttgatatg gagccaatga ctgatgcatt tttgactgct    2160
tctgttgttg ctgctgttgc taaaggcggt tcttctactt ctataactgg tattgctaac    2220
caaagagtta agaatgtaa tagaattgaa gctatggtta ctgaattggc aaaatttggt     2280
gtgccagcaa atgaattacc cgatggaatt gaaatacatg gtattgatat tgaagatttg    2340
aaaacaccag aaatttctaa agaggtgtt tcctcctatg atgatcatag agtgggtatg     2400
tcattttcat tattggcagg tttgtgtaaa gaacccgttt tgattttgga agatcaacc     2460 actggtaaga cttggccagg ttggtgggat atcttacatt ccaaatttaa gattgagctt    2520
gatggttatg aaccaccatt caatactgat aaacatgtgg ataaatctag tgataaagt     2580 atcattgtca ttggtatgag aggcactgga aaatctactt tatctgaatg gttggcttcc    2640
tttttggggt tcaagatgtt agatatggac aaatatcttg aagagaaatt gggcactggt    2700
atcaaatcat tgattaaagc caaaggttgg gaatatttcc gtcaagaaga agcaattgtt    2760
gctaaagaat gtttcaccaa gttttccaag gggtatgtac tttccactgg tggaggaatt    2820
gttgaaggtg aagatgccag acagcaattg aaatcttatg ctgataatgg agggattgtt    2880
ttgcacttgc atcgtgattt agatgaaact gtcactttct ggctgctga tacaaccaga    2940 cctgcttata gcagtgaagt tcaagaagta tggttaagaa gagaaaaatg gtaccatgaa    3000
tgttctaact accacttcta ttccagtcac tgtagtactg aggatgaatt caaccatttg    3060
agaagatcct ttgtaaacta cattaaactt atcactggtg ctgaaagacc tgttgtgcca    3120
gctggtagat cagctgctgt tgtcttgaca tcaccggatt tgaatgaagt tgttggagat    3180
ttggaatcta ttacaattgg tgctgatgca gttgaattaa gagttgattt atttaaggat    3240
acttctgctg aatttgttgc tgcccaaatt gctgtaataa gaaagcatgc cgatttacca    3300
attatttaca ctgtgagaac tgtgtcgcaa ggtggtaaat tcccagatga aaatgttgac    3360
gaattaaaga gtttgttgtt acttggtatc agattaggtg ttgcatacgt tgatcttcaa    3420
ttgactgctc cgaatgaact cattgaagag attagcagta agaagggttt cactagagtc    3480
attggtactt atcaagatat aaatggtgaa ttgaaatgga acaatgttga atggaaaaac    3540
aaatataatc aaggtgtttc catgaatgct gatattgtga gactagtcgg taaagcaaac    3600
tcaattcaag ataatttaga tttggaaaac tttaaaaagc agaatacttt aaaaccattg    3660
attgctttca atttaggttc tcaaggtaag ttgtcacaag tattgaatgg aacattcacc    3720
cctatttccc acaaattact tccaaatgat gaagagttct taacaatcgg cgaattaaat    3780
caaacttatt ttgatattgg aggtttcact gctaaaaaat ttgggtcat tggttcaccc     3840 attgaacatt caagatcacc aaacttgcac aatgcagggt ataaagcatt gaatttgcct    3900
taccaatttg gcagatttga agctacagat gttgatgttg tttatgataa cttgatcaat    3960
```

-continued

```
aaaccagact ttggtggttt agccatcact atgccattga aattggatat catgaagttt    4020
gccactaaac tatctgatgc agcagagacc attggagccg tcaacacatt gattccaatt    4080
gaaggcggat attttggtga taacactgat tgggtgggta ttagtaattc tttcataaga    4140
gcaggtgttc cacctaagct gagctcgaat gggttagttg ttggtgcagg cggcacttct    4200
agagctgcca tttatgcctt acatcaaatg ggatgtgcaa agatttactt ggtgaatcgt    4260
actgctgcta aattggagga acttgtcaag tcattcccta aagactataa tcttgagatt    4320
gtcgaaaccg aacaacaagc cgataaagca agtaaagtcc tgttggcagt gtcttgtatt    4380
cctgctgata aaccattaga tggagaagtg ttgaagaaaa ttgagcgaat tttatctaat    4440
ggaagtgaac aatctgctgg tttcaagcca accttattgg aagctagtta caaaccaaga    4500
gtgacaccaa ttatgaagct tgctgaagaa caatataaat ggaaagttat cccaggtgtt    4560
gagatgttgg taaatcaagg tgatagacag tttaaacttc atactggttt tactgcacca    4620
tatgagatta ttcatcgtgc tgttgttgag gaataa                              4656
```

<210> SEQ ID NO 2
<211> LENGTH: 1551
<212> TYPE: PRT
<213> ORGANISM: Candida albicans

<400> SEQUENCE: 2

```
Met Ser Ile Glu Lys Val Pro Ile Leu Gly Lys Glu Thr Ile His Val
 1               5                  10                  15

Gly Tyr Gly Ile Ala Asp His Ile Val Arg Glu Val Ile Ala Asn Leu
             20                  25                  30

Ala Ser Ser Thr Tyr Val Ile Val Thr Asp Thr Asn Met Ala Arg Thr
         35                  40                  45

Pro Gln Tyr Ser Lys Leu Thr Asp Asp Phe Lys Thr Asn Leu Ser Glu
     50                  55                  60

Lys Arg Pro Glu Ser Arg Leu Leu Thr Tyr Cys Val Ser Pro Gly Glu
 65                  70                  75                  80

Asn Asn Lys Asn Arg Ala Thr Lys Ala Ala Val Glu Asp Phe Leu Leu
                 85                  90                  95

Gln Gln Gly Cys Thr Arg Asp Thr Val Ile Leu Ala Val Gly Gly Gly
            100                 105                 110

Val Ile Gly Asp Met Ile Gly Phe Val Ala Ala Thr Phe Met Arg Gly
        115                 120                 125

Val Arg Val Val Gln Val Pro Thr Thr Leu Leu Ala Met Val Asp Ser
    130                 135                 140

Ser Val Gly Gly Lys Thr Ala Ile Asp Thr Pro Leu Gly Lys Asn Phe
145                 150                 155                 160

Ile Gly Ala Phe His Gln Pro Glu Tyr Val Phe Cys Asp Val Ser Phe
                165                 170                 175

Leu Glu Thr Leu Pro Ala Arg Gln Phe Ile Asn Gly Met Ala Glu Val
            180                 185                 190

Val Lys Thr Ala Ala Ile Trp Asn Glu Glu Glu Phe Thr Arg Leu Glu
        195                 200                 205

Asn Phe Ser Lys Lys Phe Leu Ser Val Val Thr Ser Lys Lys Pro Asp
    210                 215                 220

Leu Gln Ser Ile Lys Ala Glu Leu Val Lys Thr Val Leu Glu Ser Val
225                 230                 235                 240

Arg Val Lys Ala Gly Val Val Ser Ser Asp Glu Lys Glu Ala Gly Leu
                245                 250                 255
```

-continued

```
Arg Asn Leu Leu Asn Phe Gly His Thr Ile Gly His Ala Ile Glu Ala
            260                 265                 270
Val Leu Thr Pro Glu Ala Leu His Gly Glu Cys Val Ser Ile Gly Met
            275                 280                 285
Ile Lys Glu Ala Glu Leu Ser Arg Tyr Leu Gly Ile Leu Pro Pro Val
            290                 295                 300
Ala Val Ala Arg Leu Ser Lys Cys Leu Val Ala Tyr Gly Leu Pro Val
305                 310                 315                 320
Ser Ile Asp Asp Lys Glu Phe Leu Lys Lys Val Gly Pro Lys Arg His
                    325                 330                 335
Tyr Val Glu Ile Asp Ile Leu Leu Lys Lys Met Ala Ile Asp Lys Lys
            340                 345                 350
Asn Asp Gly Ser Lys Ile Arg Cys Val Leu Leu Glu Lys Ile Gly Lys
            355                 360                 365
Cys Tyr Gln Leu Lys Ala His Gln Val Ser Lys Gln Asp Leu Ser Phe
            370                 375                 380
Val Leu Thr Asp Glu Val Leu Val His Pro Phe Thr Asn Pro Pro Lys
385                 390                 395                 400
Glu Asn Ile Ile Val Pro Pro Gly Ser Lys Ser Ile Ser Asn Arg Ala
                    405                 410                 415
Leu Ile Leu Ala Ala Leu Gly Asn Gly Thr Val Arg Val Lys Asn Leu
            420                 425                 430
Leu His Ser Asp Asp Thr Lys His Met Leu Asp Ala Val Ala Ser Leu
            435                 440                 445
Lys Gly Ala Glu Ile Ser Thr Glu Asp Asn Gly Glu Thr Ile Val Val
450                 455                 460
Lys Gly Asn Gly Gly Asn Leu Val Thr Ser Gly Glu Glu Leu Tyr Leu
465                 470                 475                 480
Gly Asn Ala Gly Thr Ala Ser Arg Phe Leu Thr Thr Val Ala Ser Leu
                    485                 490                 495
Val Gly Lys Ser Gln Ala Ser Asp Asp Val Ile Leu Thr Gly Asn Ala
            500                 505                 510
Arg Met Gln Glu Arg Pro Ile Gly Pro Leu Val Asp Ala Leu Gly Ser
            515                 520                 525
Asn Gly Ser Glu Ile Glu Tyr Leu Asn Lys Gln Gly Ser Leu Pro Leu
            530                 535                 540
Lys Ile Ser Ala Gly Asn Gly Leu Lys Gly Gly Arg Ile Glu Leu Ala
545                 550                 555                 560
Ala Thr Ile Ser Ser Gln Tyr Val Ser Ser Ile Leu Met Cys Ala Pro
                    565                 570                 575
Tyr Ala Lys Glu Pro Val Thr Leu Ala Leu Val Gly Gly Lys Pro Ile
            580                 585                 590
Ser Gln Leu Tyr Ile Asp Met Thr Cys Ala Met Met Lys Ser Phe Gly
            595                 600                 605
Ile Glu Val Thr Lys Ser Thr Thr Lys Glu Tyr Thr Tyr His Ile Pro
            610                 615                 620
Lys Gly Thr Tyr Lys Asn Pro Ser Glu Tyr Val Ile Glu Ser Asp Ala
625                 630                 635                 640
Ser Ser Ala Thr Tyr Pro Leu Ala Phe Ala Ala Met Thr Gly Thr Ser
                    645                 650                 655
Cys Thr Ile Pro Asn Ile Gly Ser Ser Leu Gln Gly Asp Ala Lys
            660                 665                 670
```

-continued

```
Phe Ala Val Asp Val Leu Lys Pro Met Gly Cys Lys Val Glu Gln Thr
            675                 680                 685
Thr Thr Ser Thr Thr Val Thr Gly Pro Pro Arg Gly His Leu Lys Pro
        690                 695                 700
Leu Pro His Val Asp Met Glu Pro Met Thr Asp Ala Phe Leu Thr Ala
705                 710                 715                 720
Ser Val Val Ala Ala Val Ala Lys Gly Gly Ser Ser Thr Ser Ile Thr
            725                 730                 735
Gly Ile Ala Asn Gln Arg Val Lys Glu Cys Asn Arg Ile Glu Ala Met
            740                 745                 750
Val Thr Glu Leu Ala Lys Phe Gly Val Pro Ala Asn Glu Leu Pro Asp
            755                 760                 765
Gly Ile Glu Ile His Gly Ile Asp Ile Glu Asp Leu Lys Thr Pro Glu
            770                 775                 780
Ile Ser Lys Arg Gly Val Ser Ser Tyr Asp Asp His Arg Val Gly Met
785                 790                 795                 800
Ser Phe Ser Leu Leu Ala Gly Leu Cys Lys Glu Pro Val Leu Ile Leu
            805                 810                 815
Glu Arg Ser Thr Thr Gly Lys Thr Trp Pro Gly Trp Asp Ile Leu
            820                 825                 830
His Ser Lys Phe Lys Ile Glu Leu Asp Gly Tyr Glu Pro Pro Phe Asn
            835                 840                 845
Thr Asp Lys His Val Asp Lys Ser Ser Asp Lys Ser Ile Ile Val Ile
850                 855                 860
Gly Met Arg Gly Thr Gly Lys Ser Thr Leu Ser Glu Trp Leu Ala Ser
865                 870                 875                 880
Phe Leu Gly Phe Lys Met Leu Asp Met Asp Lys Tyr Leu Glu Glu Lys
            885                 890                 895
Leu Gly Thr Gly Ile Lys Ser Leu Ile Lys Ala Lys Gly Trp Glu Tyr
            900                 905                 910
Phe Arg Gln Glu Glu Ala Ile Val Ala Lys Glu Cys Phe Thr Lys Phe
            915                 920                 925
Ser Lys Gly Tyr Val Leu Ser Thr Gly Gly Gly Ile Val Glu Gly Glu
            930                 935                 940
Asp Ala Arg Gln Gln Leu Lys Ser Tyr Ala Asp Asn Gly Gly Ile Val
945                 950                 955                 960
Leu His Leu His Arg Asp Leu Asp Glu Thr Val Thr Phe Leu Ala Ala
            965                 970                 975
Asp Thr Thr Arg Pro Ala Tyr Ser Ser Glu Val Gln Glu Val Trp Leu
            980                 985                 990
Arg Arg Glu Lys Trp Tyr His Glu Cys Ser Asn Tyr His Phe Tyr Ser
            995                 1000                1005
Ser His Cys Ser Thr Glu Asp Glu Phe Asn His Leu Arg Arg Ser Phe
        1010                1015                1020
Val Asn Tyr Ile Lys Leu Ile Thr Gly Ala Glu Arg Pro Val Val Pro
1025                1030                1035                1040
Ala Gly Arg Ser Ala Ala Val Val Leu Thr Ser Pro Asp Leu Asn Glu
            1045                1050                1055
Val Val Gly Asp Leu Glu Ser Ile Thr Ile Gly Ala Asp Ala Val Glu
            1060                1065                1070
Leu Arg Val Asp Leu Phe Lys Asp Thr Ser Ala Glu Phe Val Ala Ala
            1075                1080                1085
Gln Ile Ala Val Ile Arg Lys His Ala Asp Leu Pro Ile Ile Tyr Thr
```

-continued

```
            1090                1095                1100
Val Arg Thr Val Ser Gln Gly Gly Lys Phe Pro Asp Glu Asn Val Asp
1105                1110                1115                1120

Glu Leu Lys Ser Leu Leu Leu Gly Ile Arg Leu Gly Val Ala Tyr
                1125                1130                1135

Val Asp Leu Gln Leu Thr Ala Pro Asn Glu Leu Ile Glu Ile Ser
            1140                1145                1150

Ser Lys Lys Gly Phe Thr Arg Val Ile Gly Thr Tyr Gln Asp Ile Asn
            1155                1160                1165

Gly Glu Leu Lys Trp Asn Asn Val Glu Trp Lys Asn Lys Tyr Asn Gln
        1170                1175                1180

Gly Val Ser Met Asn Ala Asp Ile Val Arg Leu Val Gly Lys Ala Asn
1185                1190                1195                1200

Ser Ile Gln Asp Asn Leu Asp Leu Glu Asn Phe Lys Lys Gln Asn Thr
                1205                1210                1215

Leu Lys Pro Leu Ile Ala Phe Asn Leu Gly Ser Gln Gly Lys Leu Ser
            1220                1225                1230

Gln Val Leu Asn Gly Thr Phe Thr Pro Ile Ser His Lys Leu Leu Pro
        1235                1240                1245

Asn Asp Glu Glu Phe Leu Thr Ile Gly Glu Leu Asn Gln Thr Tyr Phe
1250                1255                1260

Asp Ile Gly Gly Phe Thr Ala Lys Lys Phe Trp Val Ile Gly Ser Pro
1265                1270                1275                1280

Ile Glu His Ser Arg Ser Pro Asn Leu His Asn Ala Gly Tyr Lys Ala
            1285                1290                1295

Leu Asn Leu Pro Tyr Gln Phe Gly Arg Phe Glu Ala Thr Asp Val Asp
            1300                1305                1310

Val Val Tyr Asp Asn Leu Ile Asn Lys Pro Asp Phe Gly Gly Leu Ala
            1315                1320                1325

Ile Thr Met Pro Leu Lys Leu Asp Ile Met Lys Phe Ala Thr Lys Leu
        1330                1335                1340

Ser Asp Ala Ala Glu Thr Ile Gly Ala Val Asn Thr Leu Ile Pro Ile
1345                1350                1355                1360

Glu Gly Gly Tyr Phe Gly Asp Asn Thr Asp Trp Val Gly Ile Ser Asn
            1365                1370                1375

Ser Phe Ile Arg Ala Gly Val Pro Pro Lys Leu Ser Ser Asn Gly Leu
            1380                1385                1390

Val Val Gly Ala Gly Gly Thr Ser Arg Ala Ala Ile Tyr Ala Leu His
            1395                1400                1405

Gln Met Gly Cys Ala Lys Ile Tyr Leu Val Asn Arg Thr Ala Ala Lys
        1410                1415                1420

Leu Glu Glu Leu Val Lys Ser Phe Pro Lys Asp Tyr Asn Leu Glu Ile
1425                1430                1435                1440

Val Glu Thr Glu Gln Gln Ala Asp Lys Ala Ser Lys Val Leu Leu Ala
                1445                1450                1455

Val Ser Cys Ile Pro Ala Asp Lys Pro Leu Asp Gly Glu Val Leu Lys
            1460                1465                1470

Lys Ile Glu Arg Ile Leu Ser Asn Gly Ser Glu Gln Ser Ala Gly Phe
        1475                1480                1485

Lys Pro Thr Leu Leu Glu Ala Ser Tyr Lys Pro Arg Val Thr Pro Ile
        1490                1495                1500

Met Lys Leu Ala Glu Glu Gln Tyr Lys Trp Lys Val Ile Pro Gly Val
1505                1510                1515                1520
```

-continued

```
Glu Met Leu Val Asn Gln Gly Asp Arg Gln Phe Lys Leu His Thr Gly
            1525                1530                1535

Phe Thr Ala Pro Tyr Glu Ile Ile His Arg Ala Val Val Glu Glu
            1540            1545                1550
```

ARO1 DEHYDROQUINATE SYNTHASE OF *CANDIDA ALBICANS*

This invention relates, in part, to newly identified polynucleotides and polypeptides; variants of these polynucleotides and polypeptides; processes for making these polynucleotides and these polypeptides, and their variants; agonists and antagonists of the polypeptides; and uses of these polynucleotides, polypeptides, variants, agonists and antagonists. In particular, in these and in other regards, the invention relates to polynucleotides and polypeptides of arom, hereinafter referred to as "ARO1" and "ARO1".

BACKGROUND OF THE INVENTION

It is particularly preferred to employ candidal genes and gene products as targets for the development of antifungals. Candida spp. make up a medically important genus of microbes. They are known to produce two main types of infection, superficial infections of the mucosa and skin, and systemic infections, particularly in immuno-compromised patients, characterized by dissemination to the body tissues with poor prognosis without intervention. *C. albicans* is the principal species causing candida infections.

The frequency of *Candida albicans* infections has risen dramatically in the past 20 years. This has been attributed to an increasing population of people with weakened immune systems and the use of broad spectrum antibacterials and more interventional surgical practices. The amoury of good antifungal agents is small and resistance to existing agents is an emerging problem. This has created a demand for both new antifungal agents and diagnostic tests for this organism.

Fungi like bacteria and plants, but unlike mammals, are able to synthesize the aromatic amino acids phenylalanine, tyrosine and tryptophan. In fungi, a single polypeptide, the arom multifunctional enzyme, catalyses five consecutive reactions of the central aromatic biosynthetic pathway (Lambert et al. (1985). The 3-dehydroquinate synthase activity of the pentafunctional arom enzyme complex of *Neurospora crassa* is $Zn^{2+}$-dependent. *Biochemical Journal* 226:817–29. Duncan et al. (1987). The pentafunctional arom enzyme of *Saccharamyces cerevisiae* is a mosaic of monofunctional domains. *Biochemical Journal* 246:375–86.). Inhibition of any step catalyzed by this enzyme will prevent the synthesis of aromatic amino acids, p-aminobenzoic acid (precursor for folate) and ubiquinone. These essential metabolites are in limiting concentrations in mammalian tissues and thus inhibition of this enzyme is a valid antifungal strategy.

Clearly, there is a need for factors that may be used to screen compounds for antifungal activity and which may also be used to determine their roles in pathogenesis of infection, dysfunction and disease. There is a need, therefore, for identification and characterization of such factors which can play a role in preventing, ameliorating or correcting infections, dysfunctions or diseases.

The polypeptide of the present invention has the conserved residues, and have amino acid sequence homology to known arom multifunctional protein protein.

SUMMARY OF THE INVENTION

Toward these ends, and others, it is an object of the present invention to provide polypeptides, inter alia, that have been identified as novel ARO1 peptides by homology between the amino acid sequence set out in Table 2 and known amino acid sequences of other proteins such as *Saccharamyces cerevisiae* ARO 1 protein.

It is a further object of the invention, moreover, to provide polynucleotides that encode ARO1 polypeptides, particularly polynucleotides that encode the polypeptide herein designated ARO1.

In a particularly preferred embodiment of this aspect of the invention the polynucleotide comprises the region encoding ARO1 polypeptides in the sequence set out in Table 1 [SEQ ID NO:1], or a variant thereof.

In another particularly preferred embodiment of the present invention there is a novel arom multifunctional protein protein from *Candida albicans* comprising the amino acid sequence of Table 2 [SEQ ID NO:2], or a variant thereof.

In accordance with this aspect of the present invention there is provided an isolated nucleic acid molecule encoding a mature polypeptide expressible by the strain *Candida albicans* SC5314 contained in ATCC Deposit No. PTA-567.

In accordance with this aspect of the invention there are provided isolated nucleic acid molecules encoding ARO1, particularly Candida ARO1, including mRNAs, cDNAs, genomic DNAs and, in further embodiments of this aspect of the invention include biologically, diagnostically, prophylactically, clinically or therapeutically useful variants thereof, and compositions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of ARO1 and polypeptides encoded therefrom.

In accordance with this aspect of the invention there are provided novel polypeptides of Candida referred to herein as ARO1 as well as biologically, diagnostically, prophylactically, clinically or therapeutically useful fragments, variants thereof, and compositions comprising same.

Among the particularly preferred embodiments of this aspect of the invention are variants of ARO1 polypeptide encoded by naturally occurring alleles of the ARO1 gene.

In a preferred embodiment of this aspect of the invention there are provided methods for producing the aforementioned ARO1 polypeptides.

In accordance with yet another aspect of the present invention, there are provided inhibitors to such polypeptides, useful as antifungal agents, including, for example, antibodies.

In accordance with certain preferred embodiments of this aspect of the invention, there are provided products, compositions and methods, inter alia: assessing ARO1 expression; to treat, for example, candidosis (candidiasis), for example, superficial candidosis; candidosis of the oropharynx, such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection";

assaying genetic variation; and administering a ARO1 polypeptide or polynucleotide to an organism to raise an immunological response against a fungi, especially a Candida.

In accordance with certain preferred embodiments of this and other aspects of the invention there are provided polnucleotides that hybridize to ARO1 polynucleotide sequences.

In certain additional preferred embodiments of this aspect of the invention there are provided antibodies against ARO1 polypeptides.

In accordance with yet another aspect of the present invention, there are provided ARO1 antagonists which are also preferably fungistatic or fungicidal.

In further aspect of the invention there are provided compositions comprising a ARO1 polynucleotide or a ARO1 polypeptide for administration to a cell or to a multicellular organism.

Various changes and modifications within the spirit and scope of the disclosed invention will become readily apparent to those skilled in the art from reading the following description and from reading the other parts of the present disclosure.

TABLE 1

ARO1 cloned DNA sequence [SEQ ID NO:1]

```
   1 ATGTCTATTG AAAAGGTGCC AATTTTGGGT AAGGAAACTA TCCATGTTGG
  51 TTATGGTATT GCCGACCATA TTGTCAGGGA AGTGATAGCC AACTTGGCTT
 101 CTTCAACTTA TGTTATAGTG ACTGACACAA ACATGGCAAG AACTCCCCAA
 151 TATTCCAAAT TGACTGATGA TTTCAAAACT AATTTGTCTG AAAAACGTCC
 201 TGAATCCAGA TTATTGACTT ATTGTGTATC ACCGGGTGAA AACAACAAAA
 251 ACAGAGCTAC CAAAGCTGCA GTGGAAGATT TTCTTTTACA ACAAGGTTGT
 301 ACCAGAGACA CCGTCATATT GGCTGTTGGT GGGGGTGTTA TTGGTGACAT
 351 GATTGGGTTT GTTGCCGCCA CATTTATGAG AGGTGTCAGA GTTGTTCAAG
 401 TTCCAACTAC ATTGTTAGCC ATGGTAGATT CATCTGTTGG TGGGAAAACC
 451 GCCATTGATA CTCCATTAGG TAAGAATTTC ATTGGTGCTT TCCATCAACC
 501 CGAATACGTT TTCTGTGATG TATCCTTTTT AGAGACTTTA CCTGCTAGAC
 551 AATTTATTAA TGGTATGCT GAAGTTGTGA AAACTGCGGC CATTTGGAAT
 601 GAAGAAGAAT TCACCAGATT AGAAAACTTT TCCAAGAAGT TTCTTTCTGT
 651 CGTTACCTCC AAAAAACCAG ATTTACAGTC AATTAAGGCT GAATTAGTGA
 701 AAACCGTTTT GGAATCTGTT AGAGTGAAAG CTGGTGTTGT GTCATCTGAT
 751 GAAAAGGAAG CTGGTCTTAG AAATTTACTT AATTTTGGCC ATACTATTGG
 801 TCATGCAATT GAAGCGGTTT TAACTCCAGA AGCATTACAT GGAGAATGTG
 851 TTTCTATTGG TATGATTAAG GAAGCTGAGT TGTCTAGATA TTTGGGTATA
 901 CTACCACCTG TTGCAGTTGC CAGATTGTCG AAATGTCTCG TTGCTTACGG
 951 CTTACCTGTG TCTATTGACG ATAAAGAATT CTTGAAAAAA GTGGGACCAA
1001 AACGTCATTA TGTTGAAATC GATATTTTGT TGAAAAAAAT GGCCATTGAC
1051 AAGAAAAATG ATGGTAGTAA GATTAGATGT GTCTTGTTAG AGAAAATTGG
1101 TAAATGTTAC CAATTGAAAG CACATCAAGT ATCCAAACAA GATTTAAGTT
1151 TTGTGTTGAC TGATGAAGTG TTGGTTCACC CATTCACCAA TCCACCTAAA
1201 GAAAACATAA TTGTTCCACC TGGTTCCAAA TCTATCTCCA ATAGAGCATT
1251 GATTTTAGCT GCTTTGGGTA ATGGTACTGT TCGTGTGAAA AATTTGTTAC
1301 ATTCAGACGA TACTAAGCAT ATGTTAGATG CTGTTGCTTC TTTAAAGGGA
1351 GCTGAAATAT CCACTGAAGA TAATGGTGAA ACCATTGTAG TTAAAGGAAA
1401 TGGTGGCAAC TTGGTCACAT CTGGCGAAGA ATTGTACTTG GGTAATGCTG
1451 GTACTGCTTC CAGATTTTTG ACTACTGTAG CTTCATTAGT GGGCAAATCA
1501 CAAGCTAGTG ATGATGTTAT TTTAACTGGT AACGCAAGAA TGCAAGAAAG
1551 ACCTATTGGA CCATTAGTGG ATGCCTTGGG ATCTAATGGT TCTGAGATTG
1601 AGTATTTGAA TAAGCAGGGT TCATTGCCAT TGAAAATCAG TGCTGGCAAT
1651 GGATTGAAAG GTGGAAGAAT AGAATTGGCT GCAACAATCT CTTCGCAGTA
1701 TGTTTCTTCA ATTTTAATGT GTGCACCATA TGCTAAGGAG CCAGTTACTT
1751 TGGCTTTAGT CGGAGGTAAA CCAATTTCTC AATTATACAT AGATATGACA
1801 TGTGCAATGA TGAAATCATT TGGTATTGAA GTTACCAAAT CAACTACTAA
1851 GGAATACACC TATCATATTC CAAAGGGGAC ATACAAGAAT CCATCTGAAT
1901 ATGTCATTGA ATCAGATGCG TCATCTGCAA CTTATCCATT AGCATTTGCT
1951 GCTATGACTG GAACATCCTG TACTATTCCG AACATAGGTT CTTCCTCATT
2001 ACAAGGAGAT GCCAAATTTG CTGTTGATGT GTTGAAACCA ATGGGGTGTA
2051 AAGTTGAACA AACCACAACT TCAACAACTG TAACTGGTCC GCCGAGAGGT
2101 CACTTGAAAC CATTACCTCA TGTTGATATG GAGCCAATGA CTGATGCATT
2151 TTTGACTGCT TCTGTTGTTG CTGCTGTTGC TAAAGGCGGT TCTTCTACTT
2201 CTATAACTGG TATTGCTAAC CAAAGAGTTA AAGAATGTAA TAGAATTGAA
```

TABLE 1-continued

| ARO1 cloned DNA sequence [SEQ ID NO:1] |
|---|
| 2251 GCTATGGTTA CTGAATTGGC AAAATTTGGT GTGCCAGCAA ATGAATTACC |
| 2301 CGATGGAATT GAAATACATG GTATTGATAT TGAAGATTTG AAAACACCAG |
| 2351 AAATTTCTAA AAGAGGTGTT TCCTCCTATG ATGATCATAG AGTGGGTATG |
| 2401 TCATTTTCAT TATTGGCAGG TTTGTGTAAA GAACCCGTTT TGATTTTGGA |
| 2451 AAGATCAACC ACTGGTAAGA CTTGGCCAGG TTGGTGGGAT ATCTTACATT |
| 2501 CCAAATTTAA GATTGAGCTT GATGGTTATG AACCACCATT CAATACTGAT |
| 2551 AAACATGTGG ATAAATCTAG TGATAAAAGT ATCATTGTCA TTGGTATGAG |
| 2601 AGGCACTGGA AAATCTACTT TATCTGAATG GTTGGCTTCC TTTTTGGGGT |
| 2651 TCAAGATGTT AGATATGGAC AAATATCTTG AAGAGAAATT GGGCACTGGT |
| 2701 ATCAAATCAT TGATTAAAGC CAAAGGTTGG GAATATTTCC GTCAAGAAGA |
| 2751 AGCAATTGTT GCTAAAGAAT GTTTCACCAA GTTTTCCAAG GGGTATGTAC |
| 2801 TTTCCACTGG TGGAGGAATT GTTGAAGGTG AAGATGCCAG ACAGCAATTG |
| 2851 AAATCTTATG CTGATAATGG AGGGATTGTT TTGCACTTGC ATCGTGATTT |
| 2901 AGATGAAACT GTCACTTTCT TGGCTGCTGA TACAACCAGA CCTGCTTATA |
| 2951 GCAGTGAAGT TCAAGAAGTA TGGTTAAGAA GAGAAAAATG GTACCATGAA |
| 3001 TGTTCTAACT ACCACTTCTA TTCCAGTCAC TGTAGTACTG AGGATGAATT |
| 3051 CAACCATTTG AGAAGATCCT TTGTAAACTA CATTAAACTT ATCACTGGTG |
| 3101 CTGAAAGACC TGTTGTGCCA GCTGGTAGAT CAGCTGCTGT TGTCTTGACA |
| 3151 TCACCGGATT GAATGAAGT TGTTGGAGAT TTGAATCTA TTACAATTGG |
| 3201 TGCTGATGCA GTTGAATTAA GAGTTGATTT ATTTAAGGAT ACTTCTGCTG |
| 3251 AATTTGTTGC TGCCCAAATT GCTGTAATAA GAAAGCATGC CGATTTACCA |
| 3301 ATTATTTACA CTGTGAGAAC TGTGTCGCAA GGTGGTAAAT TCCCAGATGA |
| 3351 AAATGTTGAC GAATTAAAGA GTTTGTTGTT ACTTGGTATC AGATTAGGTG |
| 3401 TTGCATACGT TGATCTTCAA TTGACTGCTC CGAATGAACT CATTGAAGAG |
| 3451 ATTAGCAGTA AGAAGGGTTT CACTAGAGTC ATTGGTACTT ATCAAGATAT |
| 3501 AAATGGTGAA TTGAAATGGA ACAATGTTGA ATGGAAAAAC AAATATAATC |
| 3551 AAGGTGTTTC CATGAATGCT GATATTGTGA GACTAGTCGG TAAAGCAAAC |
| 3601 TCAATTCAAG ATAATTTAGA TTTGGAAAAC TTTAAAAAGC AGAATACTTT |
| 3651 AAAACCATTG ATTGCTTTCA ATTTAGGTTC TCAAGGTAAG TTGTCACAAG |
| 3701 TATTGAATGG AACATTCACC CCTATTTCCC ACAAATTACT TCCAAATGAT |
| 3751 GAAGAGTTCT TAACAATCGG CGAATTAAAT CAAACTTATT TTGATATTGG |
| 3801 AGGTTTCACT GCTAAAAAAT TTGGGTCAT TGGTTCACCC ATTGAACATT |
| 3851 CAAGATCACC AAACTTGCAC AATGCAGGGT ATAAAGCATT GAATTTGCCT |
| 3901 TACCAATTTG GCAGATTTGA AGCTACAGAT GTTGATGTTG TTTATGATAA |
| 3951 CTTGATCAAT AAACCAGACT TTGGTGGTTT AGCCATCACT ATGCCATTGA |
| 4001 AATTGGATAT CATGAAGTTT GCCACTAAAC TATCTGATGC AGCAGAGACC |
| 4051 ATTGGAGCCG TCAACACATT GATTCCAATT GAAGGCGGAT ATTTTGGTGA |
| 4101 TAACACTGAT TGGGTGGGTA TTAGTAATTC TTTCATAAGA GCAGGTGTTC |
| 4151 CACCTAAGCT GAGCTCGAAT GGGTTAGTTG TTGGTGCAGG CGGCACTTCT |
| 4201 AGAGCTGCCA TTTATGCCTT ACATCAAATG GGATGTGCAA AGATTTACTT |
| 4251 GGTGAATCGT ACTGCTGCTA AATTGGAGGA ACTTGTCAAG TCATTCCCTA |
| 4301 AAGACTATAA TCTTGAGATT GTCGAAACCG AACAACAAGC CGATAAAGCA |
| 4351 AGTAAAGTCC TGTTGGCAGT GTCTTGTATT CCTGCTGATA AACCATTAGA |
| 4401 TGGAGAAGTG TTGAAGAAAA TTGAGCGAAT TTTATCTAAT GGAAGTGAAC |
| 4451 AATCTGCTGG TTTCAAGCCA ACCTTATTGG AAGCTAGTTA CAAACCAAGA |
| 4501 GTGACACCAA TTATGAAGCT TGCTGAAGAA CAATATAAAT GGAAAGTTAT |
| 4551 CCCAGGTGTT GAGATGTTGG TAAATCAAGG TGATAGACAG TTTAAACTTC |
| 4601 ATACTGGTTT TACTGCACCA TATGAGATTA TCATCGTGC TGTTGTTGAG |
| 4651 GAATAA |

TABLE 2

| ARO1 deduced amino acid sequence [SEQ ID NO:2] |
|---|
| 1 MSIEKVPILG KETIHVGYGI ADHIVREVIA NLASSTYVIV TDTNMARTPQ |
| 51 YSKLTDDFKT NLSEKRPESR LLTYCVSPGE NNKNRATKAA VEDFLLQQGC |
| 101 TRDTVILAVG GGVIGDMIGF VAATFMRGVR VVQVPTTLLA MVDSSVGGKT |
| 151 AIDTPLGKNF IGAFHQPEYV FCDVSFLETL PARQFINGMA EVVKTAAIWN |
| 201 EEEFTRLENF SKKFLSVVTS KKPDLQSIKA ELVKTVLESV RVKAGVVSSD |
| 251 EKEAGLRNLL NFGHTIGHAI EAVLTPEALH GECVSIGMIK EAELSRYLGI |
| 301 LPPVAVARLS KCLVAYGLPV SIDDKEFLKK VGPKRHYVEI DILLKKMAID |
| 351 KKNDGSKIRC VLLEKIGKCY QLKAHQVSKQ DLSFVLTDEV LVHPFTNPPK |
| 401 ENIIVPPGSK SISNRALILA ALGNGTVRVK NLLHSDDTKH MLDAVASLKG |
| 451 AEISTEDNGE TIVVKGNGGN LVTSGEELYL GNAGTASRFL TTVASLVGKS |
| 501 QASDDVILTG NARMQERPIG PLVDALGSNG SEIEYLNKQG SLPLKISAGN |
| 551 GLKGGRIELA ATISSQYVSS ILNCAPYAKE PVTLALVGGK PISQLYIDMT |
| 601 CAMMKSFGIE VTKSTTKEYT YHIPKGTYKN PSEYVIESDA SSATYPLAFA |
| 651 AMTGTSCTIP NIGSSSLQGD AKFAVDVLKP MGCKVEQTTT STTVTGPPRG |
| 701 HLKPLPHVDM EPMTDAFLTA SVVAAVAKGG SSTSITGIAN QRVKECNRIE |
| 751 AMVTELAKFG VPANELPDGI EIHGIDIEDL KTPEISKRGV SSYDDHRVGM |
| 801 SFSLLAGLCK EPVLILERST TGKTWPGWWD ILHSKFKIEL DGYEPPFNTD |
| 851 KHVDKSSDKS IIVIGMRGTG KSTLSEWLAS FLGFKMLDMD KYLEEKLGTG |
| 901 IKSLIKAKGW EYFRQEEAIV AKECFTKFSK GYVLSTGGGI VEGEDARQQL |
| 951 KSYADNGGIV LHLHRDLDET VTFLAADTTR PAYSSEVQEV WLRREKWYHE |

TABLE 2-continued

ARO1 deduced amino acid sequence [SEQ ID NO:2]

```
1001 CSNYHFYSSH CSTEDEFNHL RRSFVNYIKL ITGAERPVVP AGRSAAVVLT
1051 SPDLNEVVGD LESITIGADA VELRVDLFKD TSAEFVAAQI AVIRKHADLP
1101 IIYTVRTVSQ GGKFPDENVD ELKSLLLLGI RLGVAYVDLQ LTAPNELIEE
1151 ISSKKGFTRV IGTYQDINGE LKWNNVEWKN KYNQGVSMNA DIVRLVGKAN
1201 SIQDNLDLEN FKKQNTLKPL IAFNLGSQGK LSQVLNGTFT PISHKLLPND
1251 EEFLTIGELN QTYFDIGGFT AKKFWVIGSP IEHSRSPNLH NAGYKALNLP
1301 YQFGRFEATD VDVVYDNLIN KPDFGGLAIT MPLKLDIMKF ATKLSDAAET
1351 IGAVNTLIPI EGGYFGDNTD WVGISNSFIR AGVPPKLSSN GLVVGAGGTS
1401 RAAIYALHQN GCAKIYLVNR TAAKLEELVK SFPKDYNLEI VETEQQADKA
1451 SKVLLAVSCI PADKPLDGEV LKKIERILSN GSEQSAGFKP TLLEASYKPR
1501 VTPIMKLAEE QYKWKVIPGV EMLVNQGDRQ FKLHTGFTAP YEIIHRAVVE
1551 E
```

The preceding tables depict certain embodiments of the invention. They are illustrative only and do not limit the invention otherwise disclosed herein.

Table 1 shows the polynucleotide sequence of *Candida albicans* ARO1 [SEQ ID NO:1].

Table 2 shows the amino acid sequence of *Candida albicans* ARO1 [SEQ ID NO:2] deduced from the polynucleotide sequence of Table 1.

GLOSSARY

The following illustrative explanations are provided to facilitate understanding of certain terms used frequently herein, particularly in the Examples. The explanations are provided as a convenience and are not limitative of the invention.

ARO1-BINDING MOLECULE, as used herein, refers to molecules or ions which bind or interact specifically with ARO1 polypeptides or polynucleotides of the present invention, including, for example enzyme substrates, cell membrane components and classical receptors. Binding between polypeptides of the invention and such molecules, including binding or binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polynucleotide sequence.

IDENTITY or SIMILARITY, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods commonly employed to determine identity or similarity between sequences include, but are not limited to those disclosed in Carillo, H., and Lipman, D., SIAM *J. Applied Math.*, 48:1073 (1988). Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol* 215: 403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS— STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626646 (1990) and Rattan et al., *Protein Synthesis: Posttranslational Modifications and Aging*, Ann. N.Y. Acad. Sci. 663: 48–62 (1992). It will be appreciated, as is well known and as noted above, that polypeptides are not always entirely linear. For instance, polypeptides may be generally as a result of posttanslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in fungal hosts such as, for example, *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S), as the term is used herein, are polynucleotides or polypeptides that differ from a reference polynucleotide or polypeptide respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. Changes in the nucleotide sequence of the variant may be silent i.e., they may not alter the amino acids encoded by the polynucleotide. Where alterations are limited to silent changes of his type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination. (3) A variant may also be a fragment of a polynucleotide or polypeptide of the invention that differs from a reference polynucleotide or polypeptide sequence by being shorter than the reference sequence, such as by a terminal or internal deletion. A variant of a polypeptide of the invention also includes a polypeptide which retains essentially the same biological function or activity as such polypeptide, e.g., proproteins which can be activated by cleavage of the proprotein portion to produce an active mature polypeptide. (4) A variant may also be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. (5) A variant of the polynucleotide or polypeptide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Among polypeptide variants in this regard are variants that differ from the aforementioned polypeptides by amino acid substitutions, deletions or additions. The substitutions, deletions or additions may involve one or more amino acids. Alterations in the of the amino acids may be conservative or non-conservative amino acid substitutions, deletions or additions. All such variants defined above are deemed to be within the scope of those skilled in the art from the teachings herein and from the art.

DETAILED DESCRIPTION OF THE INVENTION

The present invention relates to novel ARO1 polypeptides and polynucleotides, among other things, as described in greater detail below. In particular, the invention relates to polypeptides and polynucleotides of a novel ARO1 gene of *Candida albicans*, which is related by amino acid sequence homology to Saccharamyces cerevisiae ARO1 polypeptide. The invention relates especially to ARO1 having the nucleotide and encoded amino acid sequences set out in Table 1 and Table 2 respectively, and to the ARO1 nucleotide and amino acid sequences of the DNA in ATCC Deposit No. PTA-567, which is herein referred to as "the deposited strain" or as the "DNA of the deposited strain." It will be appreciated that the nucleotide and amino acid sequences set out in Tables 1 [SEQ ID NO:1] and 2 [SEQ ID NO:2] were obtained by sequencing the DNA of the deposited strain. Hence, the sequence of ARO1 of the deposited strain is controlling as to any discrepancies between it (and the sequence it encodes) and the sequences of Table 1 [SEQ ID NO:1] and Table 2 [SEQ ID NO:2].

Techniques are available to evaluate temporal gene expression in fungi, particularly as it applies to viability under laboratory and host infection conditions. A number of methods can be used to identify genes which are essential to survival per se, or essential to the establishment/maintenance of an infection. Identification of expression of a sequence by one of these methods yields additional information about its function and permits the selection of such sequence for further development as a screening target. Briefly, these approaches include:

1) Signature Tagged Mutagenesis (STM)

This technique is described by Hensel et al., *Science* 269: 400–403(1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of fungal mutants and fungi recovered from an infected hosts are detected by amplification, radiolabeling and hybridization analysis. Mutants attenuated in virulence are revealed by absence of the tag from the pool of fungi recovered from infected hosts.

In *Candida albicans*, because the transposon system is not developed, a more efficient way of creating the tagged mutants is to use the insertion-duplication mutagenesis technique as described by Morrison et al., *J. Bacteriol.* 159:870 (1984) the contents of which is incorporated by reference for background purposes.

2) In Vivo Expression Technology (IVET)

This technique is described by Camilli et al., *Proc. Nat'l. Acad. Sci. USA*. 91:2634–2638 (1994), the contents of which is incorporated by reference for background purposes. IVET identifies genes up-regulated during infection when compared to laboratory cultivation, implying an important role in infection. Sequences identified by this technique are implied to have a significant role in infection establishment/maintenance.

In this technique random chromosomal fragments of target organism are cloned upstream of a promoter-less reporter gene in a plasmid vector. The pool is introduced into a host and at various times after infection fungi may be recovered and assessed for the presence of reporter gene expression. The chromosomal fragment carried upstream of an expressed reporter gene should carry a promoter or portion of a gene normally unregulated during infection. Sequencing upstream of the reporter gene allows identification of the up regulated gene.

3) Differential display

This technique is described by Chuang et al., *J. Bacteriol.* 175:2026–2036 (1993) and Zhao et al., *Microb. Pathog.* 25:121–9 (1998), the contents of which are incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of conditional lethal mutants by transposon mutagenesis.

This technique, described by Chun and Goebl, *Genetics* 142:39–50 (1996), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, cell wall polysaccharides, monitoring reporter enzyme gene fusions which respond to known cellular stresses.

5) Generation of conditional lethal mutants by chemical mutagenesis.

This technique is described by Beckwith, J., *Methods in Enzymology* 204:3–18 (1991), the contents of which are incorporated herein by reference for background purposes. In this technique random chemical mutagenesis of target organism, growth at temperature other than physiological temperature (permissive temperature) and subsequent replica plating and growth at different temperature (e.g., 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antifungals developed to cure established and chronic infections.

6) RT-PCR

Fungal messenger RNA, preferably that of *Candida albicans*, is isolated from fungal infected tissue e.g. 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the fungal genes which are transcribed in the infected tissue. Analysis of gene transcription can be carried out at different times of infection to gain a detailed knowledge of gene regulation in fungal pathogenesis allowing for a clearer understanding of which gene products represent targets for screens for novel antifungals. Because of the gene specific nature of the PCR primers employed it should be understood that the fungal mRNA preparation need not be free of mammalian RNA. This allows the investigator to carry out a simple and quick RNA preparation from infected tissue to obtain fungal mRNA species which are very short lived in the bacterium (in the order of 2 minute halflives). Optimally the fungal mRNA is prepared from infected murine lung tissue by mechanical disruption in the presence of TRizole (GIBCO-BRL) for very short periods of time, subsequent processing according to the manufacturers of TRIzole reagent and DNAase treatment to remove contaminating DNA. Preferably the process is optimized by finding those conditions which give a maximum amount of fungal 16S ribosomal RNA, preferably that of *Candida albicans*, as detected by probing Northerns with a suitably labeled sequence specific oligonucleotide probe. Typically a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Use of the of these technologies when applied to the sequences of the present invention enables identification of fungal proteins expressed during infection, inhibitors of which would have utility in anti-fungal therapy.

Polynucleotides

In accordance with one aspect of the present invention, there are provided isolated polynucleotides which encode the ARO1 polypeptide having the deduced amino acid sequence of Table 2 [SEQ ID NO:2].

Using the information provided herein, such as the polynucleotide sequence set out in Table 1 [SEQ ID NO:1], a polynucleotide of the present invention encoding ARO1 polypeptide may be obtained using standard cloning and screening procedures, such as those for cloning and sequencing chromosomal DNA fragments from *Candida albicans* SC5314 cells as starting material, followed by obtaining a fill length clone. For example, to obtain a polynucleotide of the invention sequence, such as that sequence given in Table 1 [SEQ ID NO:1] typically a library of clones of chromosomal DNA of *Candida albicans* SC5314 in *E. coli* or some other suitable host is probed with a radiolabeled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Candida albicans* SC5314.

ARO1 polypeptides of the invention is structurally related to other proteins of the arom family, as shown by the results of sequencing the DNA encoding ARO1 polypeptide of the deposited strain. The DNA sequence thus obtained is set out in Table 1 [SEQ ID NO:1]. It contains an open reading frame encoding a protein of having about the number of amino acid residues set forth in Table 2 [SEQ ID NO:2] with a deduced molecular weight that can be calculated using amino acid residue molecular weight values well known in the art. The protein exhibits greatest homology to Saccharamyces cerevisiae ARO1 protein among known proteins. ARO1 of Table 2 [SEQ ID NO:2] has about 59.5% identity over its entire length and about 68.8% similarity over its entire length with the amino acid sequence of Saccharamyces cerevisiae ARO 1 polypeptide.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in Table 1 [SEQ ID NO:1]. It also may be a polynucleotide with a different sequence, which, as a result of the redundancy (degeneracy) of the genetic code, encodes the polypeptide of Table 2 [SEQ ID NO:2].

Polynucleotides of the present invention which encode the polypeptide of Table 2 [SEQ ID NO:2] may include, but are not limited to the coding sequence for the mature polypeptide, by itself, the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci.*, USA 86: 821–824 (1989), for instance, hexa-histidine provides for convenient purification of the fusion protein. The HA tag may also be used to create fision proteins and corresponds to an epitope derived of influenza hemagglutinin protein, which has been described by Wilson et al., *Cell* 37: 767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly fungal, and more particularly the *Candida albicans* ARO1 having the amino acid sequence set out in Table 2 [SEQ ID NO:2]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for variants of the polypeptide having the deduced amino acid sequence of Table 2 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of ARO1 set out in Table 2 [SEQ ID NO:2]; variants thereof.

Further particularly preferred in this regard are polynucleotides encoding ARO1 variants of the fragments, which have the amino acid sequence of ARO1 polypeptide of Table 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of ARO1. Also especially preferred in this regard are conservative substitutions. Most highly preferred are polynucleotides encoding polypeptides having the amino acid sequence of Table 2 [SEQ ID NO:2], without substitutions.

Further preferred embodiments of the invention are polynucleotides that are at least 70% identical over their entire length to a polynucleotide encoding ARO1 polypeptide having the amino acid sequence set out in Table 2 [SEQ ID NO:2], and polynucleotides which are complementary to such polynucleotides. Alternatively, most highly preferred are polynucleotides that comprise a region that is at least 80% identical over their entire length to a polynucleotide encoding ARO1 polypeptide of the Candida albicans DNA of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of Table 1 [SEQ ID NO:1].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding ARO1 and to isolate cDNA and genomic clones of other genes that have a high sequence similarity to the ARO1 gene. Such probes generally will comprise at least 15 bases. Preferably, such probes will have at least 30 bases and may have at least 50 bases. Particularly preferred probes will have at least 30 bases and will have 50 bases or less.

For example, the coding region of the ARO1 gene may be isolated by screening using the known DNA sequence to synthesize an oligonucleotide probe. A labeled oligonucleotide having a sequence complementary to that of a gene of the present invention is then used to screen a library of cDNA, genomic DNA or MRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, including SEQ ID NOS:3 and 4, derived from the sequences of SEQ ID NOS:1 and 2 may be used in the processes herein as described, but preferably for PCR, to determine whether or not the Candida albicans genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A deposit containing a Candida albicans stain has been deposited with the American Type Culture Collection (ATCC), 12301 Park Lawn Drive, Rockville, Md. 20852, USA, National Collections of Industrial and Marine Bacteria Ltd. (NCIMB), 23 St. Machar Drive, Aberdeen AB2 1RY, Scotland on Aug. 20, 1999 and assigned ATCC Deposit No. PTA-567. The Candida albicans strain deposit is referred to herein as "the deposited stain" or as "the DNA of the deposited strain."

The deposited material is a strain that contains the full length ARO1 DNA, referred to as "C. albicans SC5314"upon deposit.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a ARO1 polypeptide which has a deduced amino acid sequence of Glu amino acids in length, as set forth in Table 2 [SEQ ID NO:2], and has a deduced molecular weight of 169 kilodaltons.

Among the particularly preferred embodiments of the invention are polypeptides having the amino acid sequence of ARO1 set out in Table 2 [SEQ ID NO:2], and variants thereof. Alternatively, particularly preferred embodiments of the invention in this regard are polypeptides having the amino acid sequence of the ARO1, and variants thereof.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants thereof, having the amino acid sequence of the ARO1 polypeptide of Table 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the ARO1. Also especially preferred in this regard are conservative substitutions. Most highly preferred are polypeptides having the amino acid sequence of Table 2 [SEQ ID NO:2] without substitutions.

The polypeptides and polynucleotides of the present invention are preferably provided in an isolated form, and preferably are purified to homogeneity.

The polypeptides of the present invention include the polypeptide of Table 2 [SEQ ID NO:2] (in particular the mature polypeptide) as well as polypeptides which have at least 70% identity to the polypeptide of Table 2 [SEQ ID NO:2], preferably at least 80% identity to the polypeptide of Table 2 [SEQ ID NO:2], and more preferably at least 90% similarity (more preferably at least 90% identity) to the polypeptide of Table 2 [SEQ ID NO:2] and still more preferably at least 95% similarity (still more preferably at least 95% identity) to the polypeptide of Table 2 [SEQ ID NO:2] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the fall-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of ARO1, most particularly fragments of ARO1 having the amino acid set out in Table 2 [SEQ ID NO:2], and variants of the ARO1 of Table 2 [SEQ ID NO:2].

In this regard a fragment is a polypeptide having an amino acid sequence that entirely is the same as part but not all of the amino acid sequence of the aforementioned ARO1 polypeptides and variants thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a ARO1 polypeptide of the present comprised within a precursor polypeptide designed for expression in a host and having heterologous pre and pro-polypeptide regions fused to the amino terminus of the ARO1 fragment and an additional region fused to the carboxyl terminus of the fragment. Therefore, fragments in one aspect of the meaning intended herein, refers to the portion or portions of a fusion polypeptide or fusion protein derived from ARO1.

Representative examples of polypeptide fragments of the invention, include, for example, fragments from amino acid number 1–20, 21–40, 41–60, 61–80, 81–100, and 101-Glu, and any combination of these 20 amino acid fragments.

In this context "about" herein includes the particularly recited ranges larger or smaller by several, a few, 5, 4, 3, 2 or 1 amino acid at either extreme or at both extremes.

Preferred fragments of the invention include, for example, truncation polypeptides of ARO1. Truncation polypeptides include ARO1 polypeptides having the amino acid sequence of Table 2, or of variants thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally. Degradation forms of the polypeptides of the invention in a host cell, particularly a Candida, are also preferred.

Also preferred in this aspect of the invention are fragments characterized by structural or functional attributes of ARO1. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of ARO1, and combinations of such fragments.

Preferred regions are those that mediate activities of ARO1. Most highly preferred in this regard are fragments that have a chemical, biological or other activity of ARO1, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al, *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989).

Polynucleotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with procaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in procaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E. Coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating codon, for example, AUG or GUG, at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

Representative examples of appropriate hosts include bacterial cells, such as streptococci, staphylococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE-60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known procaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the codon that initiates translation of the polypeptide to be expressed, for example AUG or GUG. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al. *Journal of Molecular Recognition*, Vol. 8 52–58 (1995) and K. Johanson et al., *The Journal of Biological Chemistry*, Vol. 270, No. 16, pp 9459–9471(1995).

Cells typically then are harvested by centrifligation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

ARO1 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide Assays

This invention is also related to the use of the ARO1 polynucleotides to detect complementary polynucleotides such as, for example, as a diagnostic reagent. Detection of ARO1 polynucleotides in a eukaryote, particularly a mammal, and especially a human, will provide a diagnostic method for diagnosis of a disease. Eukaryotes (herein also "individual(s)"), particularly mammals, and especially humans, infected with an organism comprising a ARO1 polynucleotide, particularly the gene sequence may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., *Nature*, 324: 163–166 (1986) prior to analysis. RNA or cDNA may also be used in the same ways. As an example, PCR primers complementary to the nucleic acid encoding ARO1 polypeptide can be used to identify and analyze ARO1 presence and/or expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled ARO1 RNA or alternatively, radiolabeled ARO1 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g, Myers et al., *Science*, 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA*, 85: 4397–4401 (1985)).

Thus, the detection of a specific DNA sequence may be achieved by methods such as hybridization, RNase protection, chemical cleavage, direct DNA sequencing or the use of restriction enzymes, e.g, restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for stereotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding ARO1 polypeptide can be used to identify and analyze mutations. The primers may be used to amplify the gene isolated from the individual such that the gene may then be subject to various techniques for elucidation of the DNA sequence. In this way, mutations in the DNA sequence may be diagnosed.

The invention provides a process for diagnosing, disease, preferably fungal infections, more preferably *Candida albicans*, and most preferably candidosis (candidiasis), for example, superficial candidosis; candidosis of the oropharynx, such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalintis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection", comprising determining from a sample derived from an individual a increased level of expression of polynucleotide having the sequence of Table 1 [SEQ ID NO:1]. Increased expression of ARO1 polynucleotide can be measured using any on of the methods well known in the art for the quantation of polynucleotides, such as, for example, PCR, RT-PCR, RNase protection, Northern blotting and other hybridization methods.

Polypeptide Assays

The present invention also relates to a diagnostic assays such as quantitative and diagnostic assays for detecting levels of ARO1 protein in cells and tissues, including determination of normal and abnormal levels. Thus, for instance, a diagnostic assay in accordance with the invention for detecting over-expression of ARO1 protein compared to normal control tissue samples may be used to detect the presence of an infection, for example. Assay techniques that can be used to determine levels of a ARO1 protein, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to ARO1, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, and variants thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope–termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against ARO1 may be employed to inhibit and/or treat infections, particularly fungal infections and especially candidosis (candidiasis), for example, superficial candidosis; candidosis of the oropharynx such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection".

Polypeptide derivatives and variants include antigenically, epitopically or immunologically equivalent derivatives which form a particular aspect of this invention. The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al, J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

ARO1-binding Molecules and Assays

This invention also provides a method for identification of molecules, such as binding molecules, that bind ARO1 polynucleotides and polypeptides. Genes encoding proteins that bind ARO1, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991). Also, a labeled ligand can be photoaffinity linked to a cell extract.

Polypeptides of the invention also can be used to assess ARO1 binding capacity of ARO1-binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and Agonists—Assays and Molecules

The invention also provides a method of screening compounds to identify those which enhance (agonist) or block (antagonist) the action of ARO1 polypeptides or polynucleotides, such as its interaction with ARO1-binding molecules.

For example, to screen for agonists or antagonists, a synthetic reaction mix, a cellular compartment, such as a membrane, cell envelope or cell wall, or a preparation of any thereof, may be prepared from a cell that expresses a molecule that binds ARO1. The preparation is incubated with labeled ARO1 in the absence or the presence of a candidate molecule which may be a ARO1 agonist or antagonist. The ability of the candidate molecule to bind the binding molecule is reflected in decreased binding of the labeled ligand. Molecules which bind gratuitously, i.e., without inducing the effects of ARO1 on binding the ARO1 binding molecule, are most likely to be good antagonists. Molecules that bind well and elicit effects that are the same as or closely related to ARO1 are agonists.

ARO1-like effects of potential agonists and antagonists may by measured, for instance, by determining activity of a reporter system following interaction of the candidate molecule with a cell or appropriate cell preparation, and comparing the effect with that of ARO1 or molecules that elicit the same effects as ARO1. Reporter systems that may be useful in this regard include but are not limited to colorimetric labeled substrate converted into product, a reporter gene that is responsive to changes in ARO1 activity, and binding assays known in the art.

Another example of an assay for ARO1 antagonists is a competitive assay that combines ARO1 and a potential antagonist with membrane-bound ARO1-binding molecules, recombinant ARO1 binding molecules, natural substrates or ligands, or substrate or ligand mimetics, under appropriate conditions for a competitive inhibition assay. ARO1 can be labeled, such as by radioactivity or a colorimetric compound, such that the number of ARO1 molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing ARO1-induced activities, thereby preventing the action of ARO1 by excluding ARO1 from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, *J. Neurochem.* 56: 560 (1991); *OLIGODEOXY-NUCLEOTIDES AS ANTISENSE INHIBITORS OF GENE EXPRESSION*, CRC Press, Boca Raton, Fla. (1988), for a description of these molecules).

Preferred potential antagonists include compounds related to and variants of ARO1.

In a particular aspect the invention provides the use of the polypeptide, polynucleotide or inhibitor of the invention to interfere with the initial physical interaction between a fungal pathogen and mammalian host responsible for sequelae of infection. In particular the molecules of the invention may be used: i) in the prevention of adhesion of fungi, in particular Candida fungi, to mammalian extracellular matrix proteins on in-dwelling devices or to extracellular matrix proteins in wounds; ii) to block arom multifunctional protein protein-mediated mammalian cell invasion by, for example, initiating phosphorylation of mammalian tyrosine kinases (Rosenshine et al., *Infect. Immun.* 60:2211 (1992); iii) to block fungal adhesion between mammalian extracellular matrix proteins and fungal arom multifunctional protein proteins which mediate tissue damage; iv) to block the normal progression of pathogenesis in infections initiated other than by the implantation of in-dwelling devices or by other surgical techniques.

Each of the DNA sequences provided herein may be used in the discovery and development of antifungal compounds. The encoded protein upon expression can be used as a target for the screening of antifungal drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed for instance to inhibit diseases, such as, for example, candidosis (candidiasis), for example, superficial candidosis; candidosis of the oropharynx, such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meitei-sho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system, Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and fimisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection".

Vaccines

Another aspect of the invention relates to a method for inducing an immunological response in an individual, particularly a mammal which comprises inoculating the individual with ARO1, or a fragment or variant thereof, adequate to produce antibody to protect said individual from infection, particularly fungal infection and most particularly Candida infections. Yet another aspect of the invention relates to a method of inducing immunological response in an individual which comprises, through gene therapy, delivering gene encoding ARO1 polypeptide, or a fragment or a variant thereof, for expressing ARO1 polypeptide, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a ARO1 polynucleotide or protein encoded therefrom, wherein the composition comprises a recombinant ARO1 polynucleotide or protein encoded therefrom comprising DNA which codes for and expresses an antigen of said ARO1 polynucleotide or protein encoded therefrom.

A ARO1 polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. *Science* 273: 352 (1996).

Also, provided by this invention are methods using the described polynucleotide or particular fragments thereof which have been shown to encode non-variable regions of fungal cell surface proteins in DNA constructs used in such genetic immunization experiments in animal models of infection with *Candida albicans* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of *Candida albicans* infection in mammals, particularly humans.

The polypeptide may be used as an antigen for vaccination of a host to produce specific antibodies which protect against invasion of fungi, for example by blocking adherence of fungi to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain ARO1 polypeptides, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant fungi shortly before insertion of an in-dwelling device. Treatment may be continued after surgery during the in-body time of the device. In addition, the composition could also be used to broaden perioperative cover for any surgical technique to prevent Candida wound infections.

Many orthopedic surgeons consider that humans with prosthetic joints should be considered for antifungal prophylaxis before dental treatment that could produce a bacterernia. Late deep infection is a serious complication sometimes leading to loss of the prosthetic joint and is accompanied by significant morbidity and mortality. It may therefore be possible to extend the use of the active agent as a replacement for prophylactic antifungals in this situation.

In addition to the therapy described above, the compositions of this invention may be used generally as a wound treatment agent to prevent adhesion of fungi to matrix proteins exposed in wound tissue and for prophylactic use in dental treatment as an alternative to, or in conjunction with, antifungal prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 μg/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of fungi containing the arom multifunctional protein protein.

In order to facilitate understanding of the following example certain frequently occurring methods and/or terms will be described.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of sill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

Example 1

Library Production

The polynucleotide having the DNA sequence given in SEQ ID NO:1 was obtained from a library of clones of chromosomal DNA of *Candida albicans*. In some cases the sequencing data from two or more clones containing overlapping *Candida albicans* DNAs was used to construct the contiguous DNA sequence in SEQ ID NO:1. Libraries may be prepared by routine methods, for example:
Methods 1 and 2 below.

Total cellular DNA is isolated from *Candida albicans* SC5314 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bsh1235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

ARO1 Complementation Analysis

*Candida albicans* ARO1 protein is tagged and this tagged version is used in immunofluorescence studies to determine the cellular localization of the protein.

Complementation analysis is used to observe whether the *Candida albicans* ARO1 clone is able to complement a ARO1-deletion in *Candida albicans* when expressed from its native promoter (Mol Gen. Genet. 200, 500–502, 1985).

Expression of ARO1 from a *Candida albicans* promoter is performed to test for complementation (Mol Gen. Genet. 200, 500–502, 1985).

Conditional alleles of ARO1 are thereby identified and are used as a basis for a cell based screens for anti-fungal compounds.

What is claimed is:

1. An isolated polynucleotide comprising a first polynucleotide or the full complement of the entire length of the first polynucleotide, wherein the first polynucleotide is at least 95% identical to the polynucleotide of SEQ ID NO:1.

2. A vector comprising the isolated polynucleotide of claim 1.

3. An isolated host cell comprising the vector of claim 2.

4. The isolated polynucleotide of claim 1, wherein the first polynucleotide is at least 97% identical to the polynucleotide of SEQ ID NO:1.

5. The isolated polynucleotide of claim 1, wherein the first polynucleotide is at least 98% identical to the polynucleotide of SEQ ID NO:1.

6. The isolated polynucleotide of claim 1, wherein the first polynucleotide is at least 99% identical to the polynucleotide of SEQ ID NO:1.

7. The isolated polynucleotide of claim 1, wherein the first polynucleotide comprises the polynucleotide of SEQ ID NO:1.

8. A vector comprising the isolated polynucleotide of claim 7.

9. An isolated host cell comprising the vector of claim 8.

10. A process for producing a polypeptide comprising the step of culturing the host cell of claim 9, under conditions sufficient for the production of the polypeptide, wherein the polypeptide is encoded by the first polynucleotide.

11. The isolated polynucleotide of claim 7 encoding a fusion polypeptide, wherein the first polynucleotide encodes part of the fusion polypeptide.

12. An isolated polynucleotide comprising a first polynucleotide or the full complement of the entire length of the first polynucleotide, wherein the first polynucleotide encodes a polypeptide comprising the amino acid sequence set forth in SEQ ID NO:2.

13. A vector comprising the isolated polynucleotide of claim 12.

14. An isolated host cell comprising the vector of claim 13.

15. A process for producing a polypeptide comprising the step of culturing the host cell of claim 14 under conditions sufficient for the production of the polypeptide, wherein the polypeptide is encoded by the first polynucleotide.

16. The isolated polynucleotide of claim 12 encoding a fusion polypeptide, wherein the first polynucleotide encodes part of the fusion polypeptide.

17. An isolated polynucleotide comprising a first polynucleotide or the full complement of the entire length of the first polynucleotide, wherein the first polynucleotide encodes a polypeptide consisting of the amino acid sequence set forth in SEQ ID NO:2.

18. A vector comprising the isolated polynucleotide of claim 17.

19. An isolated host cell comprising the vector of claim 18.

20. A process for producing a polypeptide comprising the step of culturing the host cell of claim 16 under conditions sufficient for the production of the polypeptide, wherein the polypeptide is encoded by the first polynucleotide.

21. A method for producing antibodies in a mammal comprising:
    delivering to a tissue of the mammal a nucleic acid vector to direct expression in vivo of a polypeptide from an isolated polynucleotide of claim 12, wherein the polypeptide is effective to induce an immunological response to the polypeptide of SEQ ID NO:2; and,
    wherein the polypeptide is expressed in vivo and induces an immunological response to produce antibodies to the polypeptide of SEQ ID NO:2.

* * * * *